US008804111B2

(12) United States Patent
Golovanevsky

(10) Patent No.: US 8,804,111 B2
(45) Date of Patent: Aug. 12, 2014

(54) MULTICHIP CCD CAMERA INSPECTION SYSTEM

(75) Inventor: Boris Golovanevsky, Haifa (IL)

(73) Assignee: KLA-Tencor Corporation, Milpitas, CA (US)

( * ) Notice: Subject to any disclaimer, the term of this patent is extended or adjusted under 35 U.S.C. 154(b) by 362 days.

(21) Appl. No.: 12/244,064

(22) Filed: Oct. 2, 2008

(65) Prior Publication Data

US 2009/0091751 A1 Apr. 9, 2009

Related U.S. Application Data

(60) Provisional application No. 60/977,618, filed on Oct. 4, 2007.

(51) Int. Cl.
*G01N 21/00* (2006.01)

(52) U.S. Cl.
USPC .................. 356/237.4; 356/237.2; 356/237.6; 356/239.3; 356/491; 356/326

(58) Field of Classification Search
CPC . G01N 21/9501; G01N 21/94; G01N 21/956; G01N 21/95607; G01N 21/8806
USPC ........ 356/237.1–237.5, 614, 239.3, 491, 326; 250/201.3
See application file for complete search history.

(56) References Cited

U.S. PATENT DOCUMENTS

| | | | | |
|---|---|---|---|---|
| 4,591,901 A * | 5/1986 | Andrevski | ..... | 348/337 |
| 4,715,684 A * | 12/1987 | Gagnon | ..... | 349/8 |
| 5,548,401 A * | 8/1996 | Ozaki | ..... | 356/239.3 |
| 5,604,344 A * | 2/1997 | Finarov | ..... | 250/201.3 |
| 5,804,813 A * | 9/1998 | Wang et al. | ..... | 250/201.3 |
| 6,116,739 A * | 9/2000 | Ishihara et al. | ..... | 353/31 |
| 6,172,349 B1 * | 1/2001 | Katz et al. | ..... | 250/201.3 |
| 6,741,356 B1 * | 5/2004 | Ishiwata et al. | ..... | 356/491 |
| 6,781,127 B1 * | 8/2004 | Wolff et al. | ..... | 250/332 |
| 7,034,271 B1 * | 4/2006 | Sinclair et al. | ..... | 250/201.3 |
| 7,071,451 B2 * | 7/2006 | Ishikawa et al. | ..... | 250/201.4 |
| 7,227,113 B2 * | 6/2007 | Kitahara | ..... | 250/201.3 |
| 7,277,172 B2 * | 10/2007 | Kandel et al. | ..... | 356/369 |
| 2001/0030744 A1 * | 10/2001 | Chang | ..... | 356/237.3 |
| 2004/0124334 A1 * | 7/2004 | Kreh | ..... | 250/201.3 |
| 2006/0092426 A1 * | 5/2006 | Kamei et al. | ..... | 356/491 |
| 2006/0262275 A1 * | 11/2006 | Domroese et al. | ..... | 353/20 |
| 2006/0268402 A1 * | 11/2006 | Eustergerling et al. | ..... | 359/386 |
| 2008/0063998 A1 * | 3/2008 | Liang et al. | ..... | 433/29 |
| 2008/0090198 A1 * | 4/2008 | Liang et al. | ..... | 433/29 |
| 2008/0239458 A1 * | 10/2008 | Sachs et al. | ..... | 359/294 |

* cited by examiner

*Primary Examiner* — Tarifur Chowdhury
*Assistant Examiner* — Isiaka Akanbi
(74) *Attorney, Agent, or Firm* — Luedeka Neely Group, P.C.; Rick Barnes

(57) ABSTRACT

In one embodiment, a surface inspection system comprises a radiation source that emits a broadband radiation beam, a radiation directing assembly to target radiation onto a surface of an object, the radiation directing assembly comprising a radiation collection assembly to collect radiation reflected from the surface of the object, the radiation collection assembly comprising at least one multi-chip detector array assembly positioned within a field of view of the inspection system.

8 Claims, 3 Drawing Sheets

MULTICHIP CCD CAMERA INSPECTION SYSTEM

RELATED APPLICATIONS

This application claims the benefit of priority of U.S. Provisional Patent Application Ser. No. 60,977,618, filed Oct. 4, 2007, entitled MULTICHIP CCD CAMERA, the entire disclosure of which is incorporated herein.

BACKGROUND

The subject matter described herein relates to surface inspection techniques, and more particularly to systems and methods for wafer inspection that utilize charge-coupled device (CCD) cameras that include multiple CCD chips, or single CCD chips which have been subdivided into multiple chips.

Semiconductor materials may be inspected for defects such as, e.g., surface imperfections, particles, irregularities in the thickness of thin film coatings, and the like, which may hamper the performance of the semiconductor material. Some existing inspection systems direct a beam of radiation on the surface of the semiconductor material, then collect and analyze light reflected and/or scattered from the surface to quantify characteristics of the surface.

Additional inspection techniques are desirable. Although CCD type of image sensors are described herein, other type of imaging sensor (CMOS for instance) may be used in multi chip approach for most of the applications.

DETAILED DESCRIPTION

Described herein are exemplary techniques to implement multi-CCD cameras in wafer inspection system and methods. Throughout this document, terms like light, optical, optics, rays and beams with reference to electromagnetic radiation may be used with no implication that the radiation is or is not in the visible portion of the spectrum. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Figure 1:
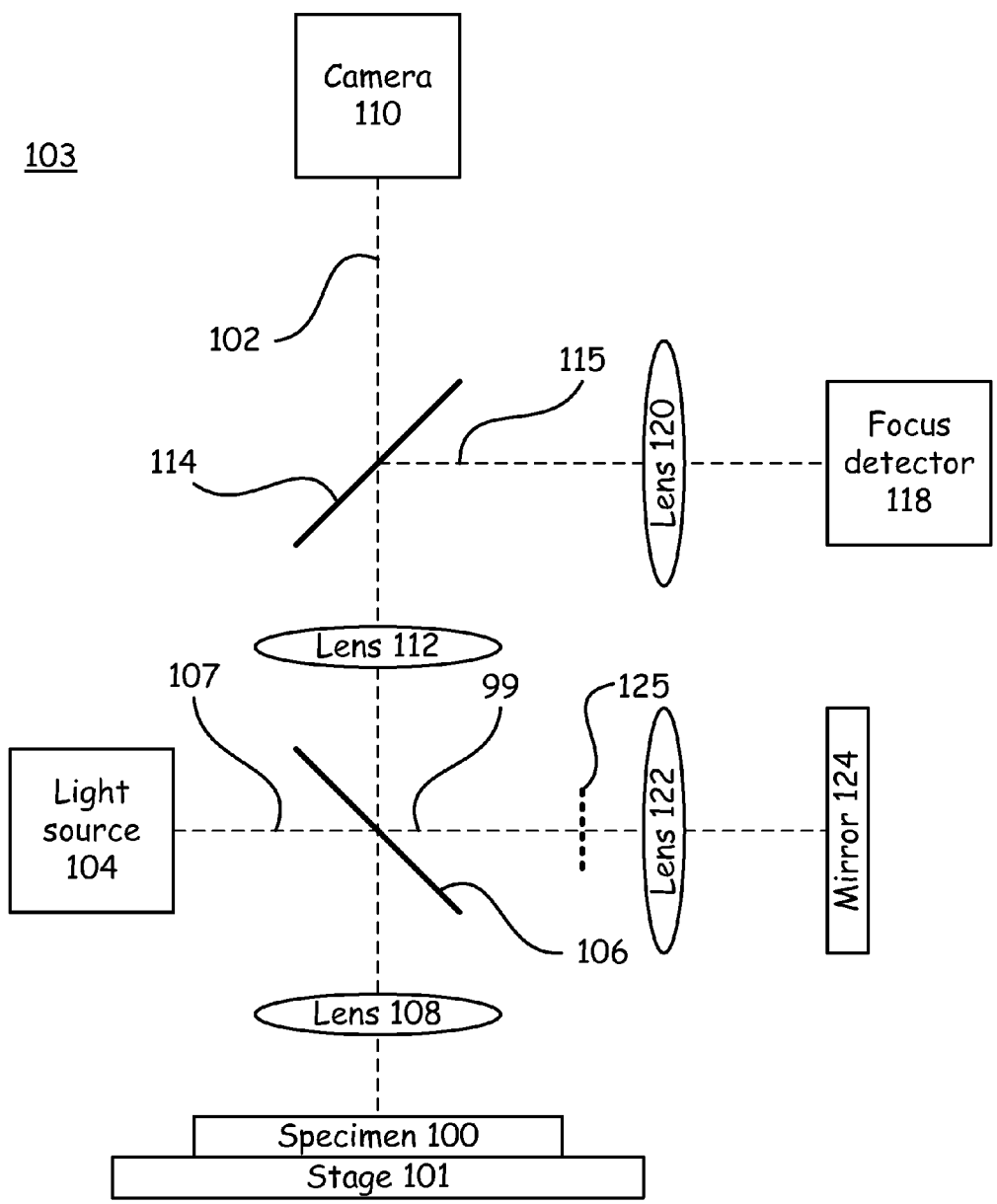
FIG. 1 is a schematic illustration of an inspection system, according to embodiments.

FIG. 1 is a schematic representation of a coherence microscope system 103. Some, but not all portions of the coherence microscope system of the present invention are described in U.S. Pat. Nos. 4,818,110 and 6,172,349, the disclosures of which are incorporated by reference herein. In one embodiment 103, a specimen 100 is disposed on a computer-controlled motorized and metered x-y (z) stage 101 and is mounted so as to lie perpendicular to a main optical axis 102 of the microscope system 103. A light source 104 provides a beam 107 of broadband illumination that impinges on the specimen 100 via a beam splitter 106 and an objective lens 108. The light reflected by the specimen 100 travels to a camera 110 via objective lens 108, beam splitter 106, pupil control optics 112, and a beam splitter 114. The camera 110 generates video data, corresponding to the inspected surface area of the wafer 100.

Part of the light reflected from the specimen 100 is split off by the beam splitter 114 and directed along a secondary path 115 and imaged onto a focus detector 118 by a lens 120. To allow the system 103 to function as a Linnik microscope, a reference light path 99, colinear with the source beam path 107, passes through lens 122 and reflects off planar mirror 124, providing a reference wavefront to both the camera 110 and the focus detector 118 by means of beam splitters 106 and 114. The reference path 99 may be blocked by a shutter 125. When the shutter 125 blocks the reference path 99 the system 103 functions as a conventional microscope.

In some embodiments, the image sensor 110 is implemented as a CCD camera, and may in some embodiments be implemented as a multi-chip CCD camera. For example, in some applications color CCD cameras called 3CCD cameras may be implemented. The 3CCD cameras have three separate CCDs, each one taking a separate measurement of red, green, and blue light. Light coming into the camera is split by a trichroic prism assembly, which directs the appropriate wavelength ranges of light to their respective CCDs. The 3CCD cameras are generally regarded to provide superior color image quality to cameras with single CCD and Bayer (or other type) filters to create color images. OVL applications don't required color images. Thus, the various spectral bands may be used to improve the image contrast. At very broadband illumination, usually some wavelengths create image with opposite contrast to the rest wavelengths. If this happens, the resulting broadband image has certain contrast degradation. In order to avoid this degradation, OVL tools may implement an illuminator with set of color filters to choose the appropriate band. Some drawbacks associated with this approach are longer recipe train time (i.e., the time required measurement for all filters and choosing the best one according to some criteria) and more significant—it allows to measure only one band (color) at the time and also the light throughput is significantly lower. In case of multichip camera with specific band for each chip, the greatest flexibility could be achieved. A multi-chip CCD camera allows to measure all bands together and also include/exclude specific band/s. Thus the maximum contrast could be achieved with minimum light throughput reduction. The multi-chip camera may have any number of chips for any wavelength bands. The wavelength selection could be based on filter, hot mirrors or prism/grating wavelength separation.

Figure 2:
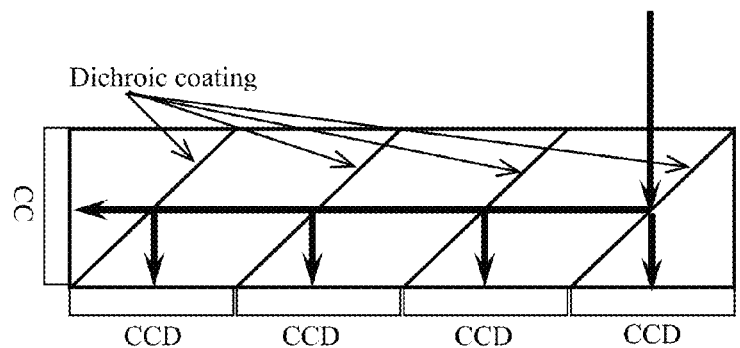
FIG. 2 is a schematic illustration of a multi-chip CCD camera that includes five CCD chips.

FIG. 2 is a schematic illustration of a multi-chip CCD camera that includes five CCD chips and using a penta-chroic prism for wavelength separation. In some embodiments the design on prisms for wavelength separation is much more complicated. In general, such prism should fulfill the following basic aspects:

All output images should be oriented in the same direction as the input image;
All channels must have the same optical path length;
The prism transmission should handle all polarizations with good uniformity;
All coatings should be protected from the environment.

Figure 3:
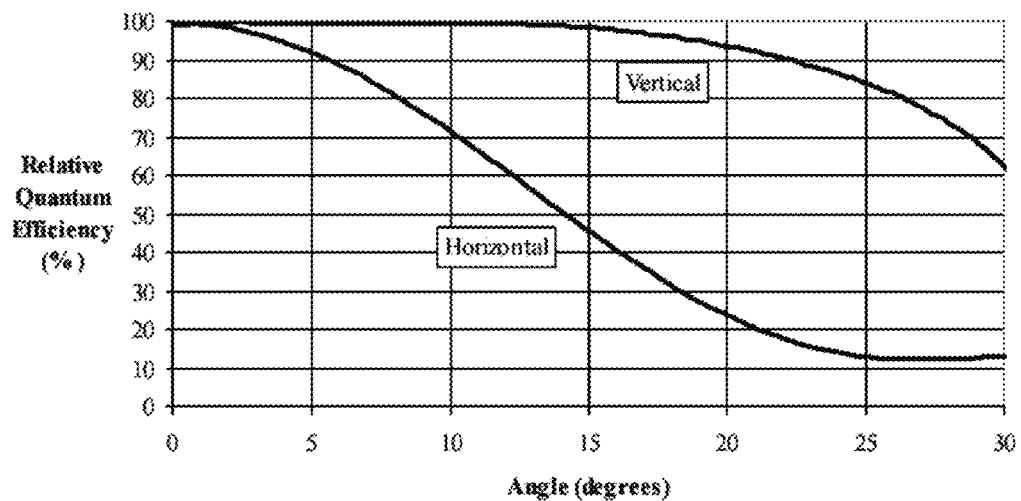
FIG. 3 is a graph which illustrates the angular quantum efficiency for a CCD, according to embodiments.
Figure 4:
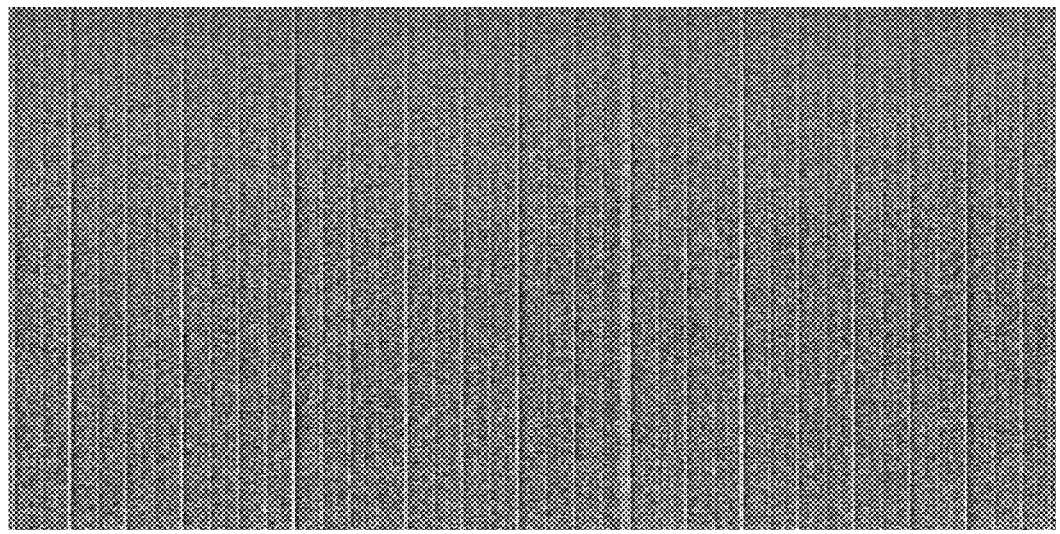
FIG. 4 is a schematic illustration of a pattern noise for a CCD, according to embodiments.
Figure 5:
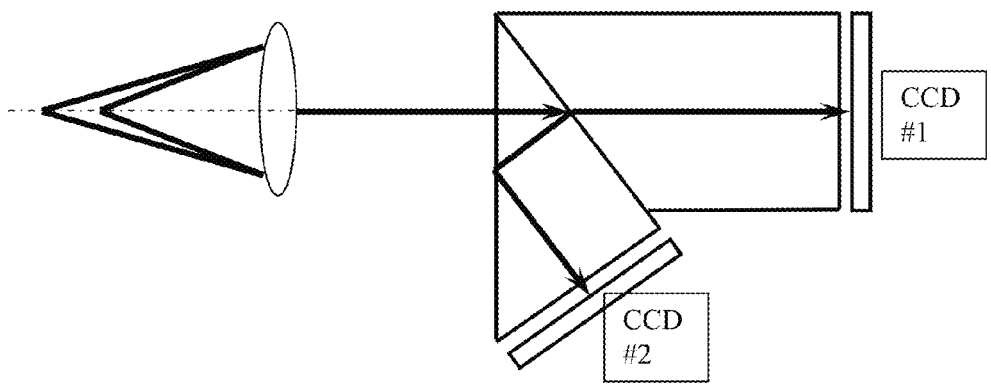
FIG. 5 is a schematic illustration of a two-chip CCD camera, according to embodiments.

At each specific case the aspects may be slightly different. A multi-chip camera may use any type of CCD, however the cheapest and the most popular CCD type is an interline transfer CCD. The interline transfer CCD camera has the widest selection on the market. It is extensively used in various machine vision applications including OVL. The interline CCD is relative cheap and fast device with good SNR and doesn't required mechanical shutter. One of the disadvantages of the interline CCD is the inherent difference between column and rows behavior. It means mainly the difference in angular quantum efficiency and fix pattern noise or PRNU (Photo Response Non Uniformity) (see FIG. 3). Thus, there are some differences in X and Y OVL measurements, which are pronounced in X/Y matching and X/Y TIS (Tool Induced Shift) issue. All these problems could be minimized by calibrations+algorithms, however the proposed embodiments allows eliminating these problems.

In one embodiment a multi-chip CCD camera may be used to implement multi-focal measurement. In some wafer inspection applications, such as overlay measurements, there are at least two different layers of the wafer that should be measured. When a high NA optics (and consequently shallow dept of focus) used and the measured layers are too thick, focus on the same location but on two different layers of the wafer is required. For automated, high-volume operation, refocusing is time-consuming. A multi-CCD camera having different focal lengths allows simultaneous acquisition of a number of images at different (fixed) focal positions. Using two separate cameras may permit relative movement between cameras. This movement may be originated from any mechanical vibration or/and difference in the thermal expansion of mechanical structure used in this arrangement. The multi-chip camera approach eliminates this issue by using a specially designed prism, where the CCD chips are glued to the prism by an index-matched optical epoxy. The thermal expansion coefficient of glass is extremely low and matches the CCD chip thermal expansion coefficient.

In another embodiment a multi-chip CCD camera may be used to obtain faster contrast focus measurements. Contrast focus measurement is time-consuming due to necessity of through focus scan with certain step and image acquisition at each step. In some embodiments, the subject matter described herein enables speeding the focusing in the number of the following ways: First, CCDs may be located at predefined focal positions to reduce number of scan steps. Different focal positions may be also achieved by using for example different glass thickness. Second, the CCDs may be located at predefined focal positions and used the different colors for each CCD.

Further, one problem in contrast focus measurement is the speed of the focus scan. It is usually limited by light throughput for high camera frame rate. One of the ways to overcome this problem is to use Xe arc lamp that have a huge intensity peaks in near infra-red (NIR). The multi-chip CCD camera approach enables the use of wide VIS band for OVL measurement and narrow one (or more) NIR band(s) for contrast focus measurement with high frame rate. For example, embodiments could include a prism with a dichroic optical coating (hot mirror) to divide the broadband spectrum into visible (let say up to 800 nm) and above (NIR).

In another embodiment, the multi-chip CCD camera may be used to multiply the total frame rate and use the band selection in illumination components of an optical system, rather than in collection components of an optical system.

In another embodiment, a multi-chip CCD camera may be used to increase dynamic range. For example, when one of the layers is bright and the other is dark ND (or color) filters with different transparency may be used in front of CCDs to enable collecting the bright picture and dark picture at once and to optimize light for the inner and the outer separately. Other embodiments may use different settings for the two chips instead of ND filters. For example two different gains or exposure/frame rate.

In another embodiment, an optical inspection system may use a beam splitter that split incoming light for the two CCD unequally (i.e., 25/75% rather than 50/50%). In another embodiment, a multi-chip CCD camera may be used for multi-band measurement. For example, a multi-chip CCD camera objective may be configured to have low chromatic aberration in a number of narrow bands that have a different focal position than optimize for one wide band to have a single focus point. A multi-chip CCD camera enables simultaneous acquiring of images for each band at the camera's best focal position. The bands may be divided like UV, Visible and NIR or Visible and NIR (for ACL layer) or any other arrangement. Due to the fact that the pictures are acquired simultaneously in the best focus for each color, the optimum color may be chosen for the inner and the outer separately.

In another embodiment, a multi-chip CCD camera may be used to increase the image contrast. The nature of OVL measurement allows the substitution of 2D searching problem with two independent 1D searching problems. It is possible not only by algorithm but also in the physical meaning. For example, a multi-chip CCD camera may be used to simultaneous acquire two images with the two polarizations (S and P) for separate X and Y OVL measurements (e.g., using unpolarized light for target illumination and linear polarizer with corresponding orientation in front of each CCD chip).

A multi-chip CCD camera may also use structured illumination with polarization to enhance dept of focus and contrast. For example: using vertical dipole illumination with vertical polarization for X OVL measurement on grating target and horizontal dipole illumination with horizontal polarization for Y OVL measurement correspondently. In this case one image will be used for X measurement and other for Y.

In another embodiment, a multi-chip CCD camera may be used to improve X-Y OVL matching. Using two CCDs with orthogonal orientation to allow optimal chip orientation for separate X/Y OVL measurements. The information redundancy presented in two images could be use to improve precision.

In another embodiment, a multi-chip CCD camera may be used to improve X-Y OVL matching and to increase the contrast focus speed, as described above.

In order to make contrast focus each CCD chip will perform linear (vertical) binning. Thus, output of each CCD will be only one row per frame. Due to the orthogonal chips orientation, it will be measure simultaneously two orthogonal lines; which will be use for fast contrast focus. On-chip line binning significantly increase detector sensitivity, reduce readout noise and therefore usually used to produce extremely high frame rate or to measure in very low light condition. Consequently, on-chip line binning allows increasing the frame rate for the same light condition without sacrificing the SNR. In this arrangement the came CCDs will be used for the fast contrast focus measurement (line detector mode—single line per frame) and for X/Y OVL measurement (area detector mode—full frame) without any improvement in light throughput.

Figure 6:
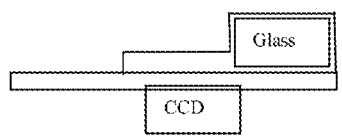
FIG. 6 is a schematic illustration of a trifocal arrangement using a single CCD chip, according to embodiments.

In most cases where a multi-chip CCD is used, the same effect could be achieved by virtually subdividing the single chip into different areas, with or without a separate readout. For example, a single chip may be subdivided into separate areas, for example, in three different areas horizontally. The difference in the focus position may be achieved by creating an optical path difference for each chip area, for example by using an optical glass with different thickness (or refractive coefficient) glued to the corresponding area of the chip. Such an arrangement is depicted in FIG. 6, in which three different glasses are interposed in the optical path of the CCD.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment. Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A surface inspection system, comprising:
   a radiation source that emits a broadband radiation beam,
   a radiation directing assembly to target the broadband radiation beam onto the surface,
   a radiation collection assembly to collect radiation reflected from the surface,
   a multi-chip detector array, comprising,
      a prism to divide the collected radiation into a first visible radiation band that exits the prism on a first face of the prism, and a second infrared and above radiation band that exits the prism on a second face of the prism that is different from the first face of the prism,
      a first chip glued to the first face of the prism by an index matched optical epoxy, the first chip to receive only the first radiation band and produce an image of the surface, and
      a second chip glued to the second face of the prism by an index matched optical epoxy, the second chip to receive only the second radiation band and produce focus data for the radiation collection assembly,
   where a thermal expansion coefficient of the prism substantially matches a thermal expansion coefficient of both the first chip and the second chip.

2. The surface inspection system of claim 1, wherein the multi-chip detector array assembly is used for simultaneous multi-focal measurement.

3. The surface inspection system of claim 1, wherein the multi-chip detector array assembly is used to increase a speed of a contrast focus measurement.

4. The surface inspection system of claim 1, wherein the multi-chip detector array assembly is used to increase a dynamic range of an image registration system.

5. The surface inspection system of claim 1, wherein the multi-chip detector array assembly is used for multi-band (color) measurement.

6. The surface inspection system of claim 1, wherein the multi-chip detector array assembly is used to increase the image contrast by simultaneously acquiring two images with two polarizations for separate X and Y OVL measurements.

7. The surface inspection system of claim 6, wherein the multi-chip detector array assembly is used to enhance depth of focus and contrast by using structured illumination with polarization.

8. The surface inspection system of claim 1, wherein the multi-chip detector array assembly is used to improve X-Y OVL matching.

* * * * *